(12) United States Patent  
Suzuki et al.

(10) Patent No.: US 8,761,483 B2  
(45) Date of Patent: Jun. 24, 2014

(54) CALIBRATION SYSTEM FOR FOCAL SPOT SHIFT IN AN X-RAY CT DEVICE

(75) Inventors: Atsuro Suzuki, Hitachi (JP); Fumito Watanabe, Kashiwa (JP); Hironori Ueki, Hachioji (JP); Yasutaka Konno, Saitama (JP); Shinichi Kojima, Hitachinaka (JP); Yushi Tsubota, Hitachi (JP)

(73) Assignee: Hitachi Medical Corporation, Tokyo (JP)

( * ) Notice: Subject to any disclaimer, the term of this patent is extended or adjusted under 35 U.S.C. 154(b) by 107 days.

(21) Appl. No.: 13/390,752

(22) PCT Filed: Aug. 12, 2010

(86) PCT No.: PCT/JP2010/063714  
§ 371 (c)(1),  
(2), (4) Date: Feb. 16, 2012

(87) PCT Pub. No.: WO2011/036961  
PCT Pub. Date: Mar. 31, 2011

(65) Prior Publication Data  
US 2012/0177272 A1    Jul. 12, 2012

(30) Foreign Application Priority Data

Sep. 28, 2009    (JP) .................................. 2009-223335

(51) Int. Cl.  
*G06K 9/00*    (2006.01)

(52) U.S. Cl.  
USPC ........................................................ 382/131

(58) Field of Classification Search  
None  
See application file for complete search history.

(56) References Cited

U.S. PATENT DOCUMENTS

| | | | |
|---|---|---|---|
| 5,550,886 A * | 8/1996 | Dobbs et al. ..................... 378/19 |
| 6,014,420 A * | 1/2000 | Ooi .................................. 378/19 |
| 6,094,469 A * | 7/2000 | Dobbs et al. ..................... 378/19 |
| 7,912,270 B2 * | 3/2011 | Skinner et al. ................. 382/131 |
| 8,199,624 B2 * | 6/2012 | Matsuda ..................... 369/53.28 |
| 8,285,020 B2 * | 10/2012 | Gkanatsios et al. .......... 382/128 |
| 2004/0016885 A1 * | 1/2004 | Ikhlef ............................ 250/367 |
| 2008/0037851 A1 * | 2/2008 | Takayama ..................... 382/131 |
| 2008/0128631 A1 * | 6/2008 | Suhami ..................... 250/370.09 |
| 2008/0298193 A1 * | 12/2008 | Matsuda ..................... 369/53.28 |
| 2009/0173887 A1 * | 7/2009 | Ito et al. ................. 250/396 ML |
| 2010/0263709 A1 * | 10/2010 | Norman et al. ............... 136/246 |
| 2010/0329528 A1 * | 12/2010 | Hajnal et al. .................. 382/131 |
| 2012/0177272 A1 * | 7/2012 | Suzuki et al. ................. 382/131 |
| 2012/0278055 A1 * | 11/2012 | Schweizer et al. ............. 703/11 |
| 2013/0131438 A1 * | 5/2013 | Brewer et al. .................. 600/28 |
| 2013/0154639 A1 * | 6/2013 | Oh et al. ....................... 324/309 |

FOREIGN PATENT DOCUMENTS

| | | |
|---|---|---|
| JP | 06-269443 A | 9/1994 |
| JP | 10-234724 A | 9/1998 |
| JP | 2000-033085 A | 2/2000 |
| JP | 2000-093418 A | 4/2000 |

* cited by examiner

Primary Examiner — Tahmina Ansari  
(74) Attorney, Agent, or Firm — Mattingly & Malur, PC

(57) ABSTRACT

In a state where a subject 5 is not present, a pre-processing unit 7 changes the focal spot position that becomes the position of an X-ray tube 2, acquires the X-ray incidence rate of each detection module at each focal spot position, approximates the X-ray incidence rate of each detection module by the X-ray incidence rate of a module in which a reference detector is present, and stores the coefficient of an approximate polynomial in a storage unit 8. When a scanning of the subject 5 is performed, the X-ray incidence rate of each detection module is calculated using the X-ray incidence rate of the module in which the reference detector is present and the stored coefficient, and sensitivity correction data relating to each focal spot position is obtained using the calculated X-ray incidence rate when the scanning of the subject is performed.

5 Claims, 12 Drawing Sheets

CALIBRATION SYSTEM FOR FOCAL SPOT SHIFT IN AN X-RAY CT DEVICE

FIELD OF THE INVENTION

The present invention relates to an X-ray CT device that corrects a sensitivity change caused by movement of a focal spot.

DESCRIPTION OF THE RELATED ART

The X-ray CT (Computed Tomography) is a method for obtaining a tomography-image (X-ray absorption coefficient image) of a subject by reconstructing X-Ray projection data using a computer. As X-rays with which the subject is irradiated, a characteristic X-ray and a continuous X-ray that are generated when a target metal is bombarded by an electron beam are used. In this case, the instrument (for example, target metal) expands thermally due to energy given by the electron beam, and a focal spot that is a generation position of the X-ray may move toward an axial direction. According to the movement of the focal spot, an irradiation area of the X-ray also moves.

As a problem associated with the movement of the focal spot, other than the movement of the focal spot, there are artifacts in edge slices of an image when a detector is misaligned in the axial direction. If a position of the focal spot is fixed, a change of X-ray incidence rate due to misalignment of the detector can be corrected by a sensitivity correction data. Here, the X-ray incidence rate is a ratio of an actual X-ray dose entering into a detector to the X-ray dose to be irradiated in the detector field seen from a focal spot when a subject is absent. For example, if there is a collimator in the detector field seen from the focal point, the X-ray incidence rate becomes less than 100%.

Here, as a source of the X-ray, an X-ray tube that generates X-rays by bombarding an anode (target metal) with electrons that are accelerated by high voltage is generally used. However, X-ray generation efficiency against the energy used for the acceleration of the electrons is low, and most of the energy is transformed into heat, and as a result, a displacement of the X-ray generation position (focal spot position) may be caused by thermal expansion of the heated anode (target metal). In addition, since the X-ray tube is installed in a gantry that moves and rotates, a position of the X-ray tube shifts in accordance with the movement and rotation of the gantry, and as a result, the focal spot position may be changed. Therefore, a mismatch of a focal spot position between measurement of sensitivity collection data and patient (subject) data causes the X-ray incidence rate change in the detector, and as a result, the sensitivity correction becomes incomplete and artifact is generated in the image. Broadening an aperture width of a collimator can reduce the artifacts. However, the ineffective exposure may be caused.

As a countermeasure of the foregoing problem, as described in Patent Document 1 or Patent Document 2, there is a method for correcting the X-ray detector sensitivity, where a focal spot moving area is divided into several small areas, an X-ray detector sensitivity correction data is acquired and stored for each small area in advance, and the X-ray detector sensitivity is corrected by using the X-ray detector sensitivity correction data corresponding to the focal spot position when the subject data are measured.

As another problem associated with the movement of the focal spot position, there is artifact generated in all slices of image when a two-dimensional grid that removes scattered rays of the subject is used.

As a countermeasure of the foregoing problem, as described in Patent Document 3, there is a method to move a non-sensitive area in accordance with the focal spot position that is acquired by the measurement, by disposing a plurality of X-ray detectors that are smaller than a collection pitch in the slice direction between the grids.

PRIOR ART DOCUMENT

Patent Document

[Patent Document 1] Japanese Patent Publication No. 06-269443
[Patent Document 2] Japanese Patent Publication No. 10-234724
[Patent Document 3] Japanese Patent Publication No. 2000-93418

SUMMARY OF THE INVENTION

Problems to be Solved by the Invention

However, in the methods described in Patent Document 1 and Patent Document 2, since the sensitivity correction data is discrete while the movement of the focal spot that is an X-ray source is continuous, accuracy of the correction is degraded.

In addition, since the sensitivity correction data corresponding to the focal spot position are required for each detector, the number of data to be stored in a storage provided in an X-ray CT device becomes huge.

In addition, in the method described in Patent Document 3, since a plurality of detectors that are smaller than the actual collection pitch are required, the number of signals to be processed associated with the plurality of detectors increases, and the total device configuration becomes complex.

The present invention has been developed in consideration of the foregoing problems, and it is, therefore, an object of the present invention to provide an X-ray CT device that can estimate a sensitivity correction data under the condition that a focal spot position is moved, with high accuracy and simple processing.

Means for Solving the Problems

In order to achieve the foregoing object, according to the present invention, there is provided an X-ray CT device which includes: an X-ray tube that radiates an X-ray; a collimator that limits an irradiation area of the X-ray; at least one detection module that has a plurality of detectors for detecting the X-ray; a grid that is disposed in the plurality of detectors and removes scattered rays from a subject when the X-ray is radiated on the subject; a storage unit; a pre-processing unit that prepares a sensitivity correction data based on an output of the plurality of detectors; an image reconstruction processing unit that corrects the output of the plurality of detectors by using the sensitivity correction data and reconstruct an image of the subject based on the corrected output; and an image display unit that displays the image reconstructed by the image reconstruction processing unit. The pre-processing unit includes: means for acquiring an X-ray incidence rate of each detection module at each focal spot position by changing the focal spot position that is a position of the X-ray tube under the condition that the subject is absent; means for acquiring a relationship between a reference signal and the acquired X-ray incidence rate of each detection module under the condition that the subject is absent; means for storing the acquired relationship in the storage unit; means for calculating the X-ray incidence rate of each detection module during the subject scan by using the reference signal during the subject scan and the stored relationship; and means for acquiring the sensitivity correction data of each focal spot position by using the calculated X-ray incidence rate during the subject scan.

Effects of the Invention

According to the present invention, a sensitivity correction data under the condition that a focal spot position is moved can be estimated with high accuracy and simple processing.

EMBODIMENT FOR EMBODYING THE INVENTION

First Embodiment

Hereinafter, explanations will be given in detail of preferred embodiments of the present invention by referring to accompanying drawings. Meanwhile, in the explanations below and in the accompanying drawings, a constituent having substantially an identical function is given the same reference, and a duplicate explanation will be omitted.

Figure 1:
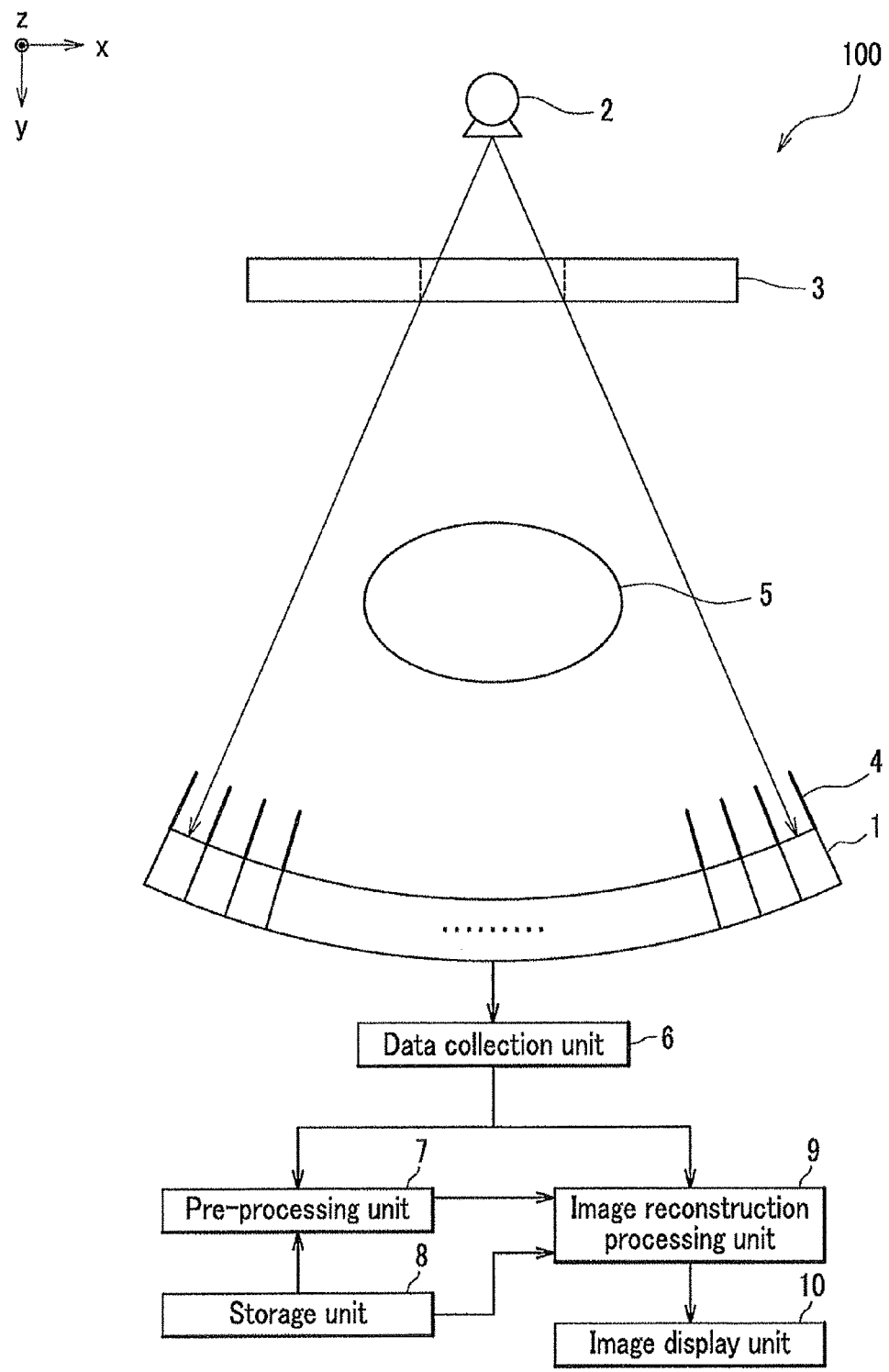
FIG. 1 is a schematic configuration view of an X-ray CT device according to a first embodiment of the present invention.

FIG. 1 is a schematic configuration view of an X-ray CT device 100.

The X-ray CT device 100 includes a detector 1, an X-ray tube 2, a collimator 3, a one-dimensional grid 4, a data collection unit 6, a pre-processing unit 7, a storage unit 8, an image reconstruction processing unit 9, and an image display unit 10.

The X-ray tube 2 radiates an X-ray. The X-ray tube 2 generates the X-ray by bombarding an anode (target metal) with electrons that are accelerated by high voltage. In the explanations below, the X-ray tube 2 is also called a focal spot, and the position thereof is called a focal spot position. The collimator 3 limits the radiated X-ray within a predetermined irradiation area (for example, a beam shape). The X-ray whose irradiation area is limited by the collimator 3 passes through a subject 5 and bed (not shown).

The one-dimensional grid 4 removes scattered rays in x-direction that are generated from the subject 5. The detector 1 detects the X-ray passed through the subject 5. The data collection unit 6 converts an output of the detector 1 from analog signal to digital signal. The pre-processing unit 7 estimates a sensitivity correction data corresponding to a focal spot position. The storage unit 8 stores a relationship between an X-ray incidence rate in a reference detector that detects an X-ray that does not pass through the subject 5 and X-ray incidence rates in other detectors. The image reconstruction processing unit 9 performs an image reconstruction calculation after performing various kinds of correction processing, such as a sensitivity correction and CT value adjustment for the collected data. The image display unit displays a reconstructed image.

In the X-ray CT device 100, the subject 5 is scanned as follows.

An X-ray generated by the X-ray tube 2 is detected by the detector 1 after the X-ray passed through the subject 5. From the incident X-ray dose at the time and the X-ray dose detected by the detector 1, an attenuation rate D of the X-ray of the subject 5 is calculated. The attenuation rate D of the X-ray that passes through the subject 5 is expressed by an exponential function as follows.

$$D = \exp\{-\int \mu \cdot dL\} \quad \text{Formula 1}$$

Here, "is an attenuation coefficient of the subject 5, and a line integration of the exponential function is calculated along a straight line between a position of the X-ray tube 2 (X-ray generation position) and the detector 1. Therefore, by taking logarithm of the attenuation rate D, a profile of the integration value of the attenuation coefficient" in a certain direction can be calculated. In addition, through measurement of the X-ray by rotating the X-ray tube 2 and the detector 1 around the subject 5, profiles of the integration value of the attenuation coefficient "in all directions can be calculated. By reconstructing the image using these profiles, a distribution of the attenuation coefficient" in the subject 5 can be obtained as a tomography image.

Next, explanations will be given of a method for estimating a sensitivity correction data corresponding to a focal spot position that is executed in the pre-processing unit 7.

Figure 2:
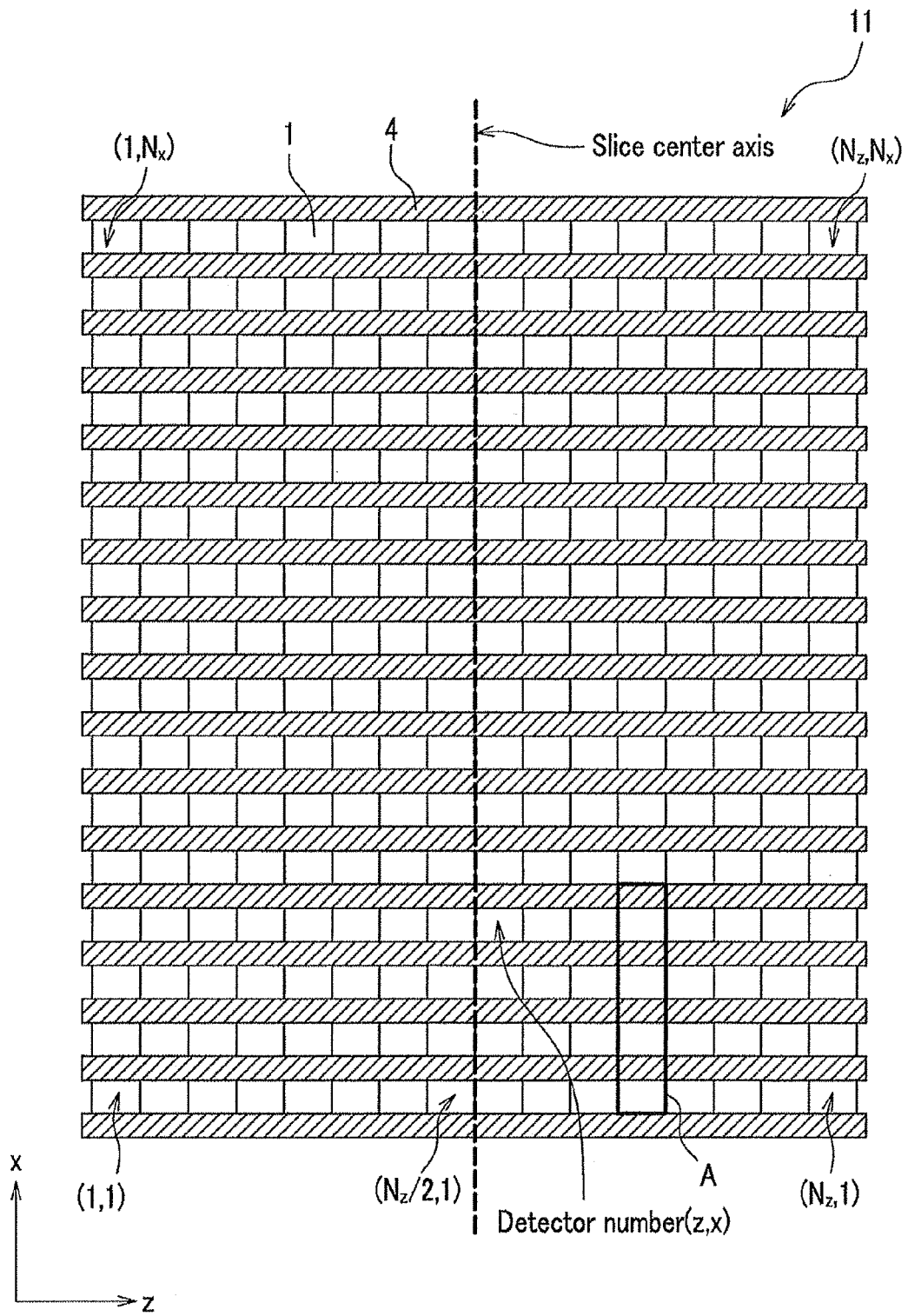
FIG. 2 is an illustration showing a module configured by detectors and a one-dimensional grid according to the first embodiment.
Figure 3:
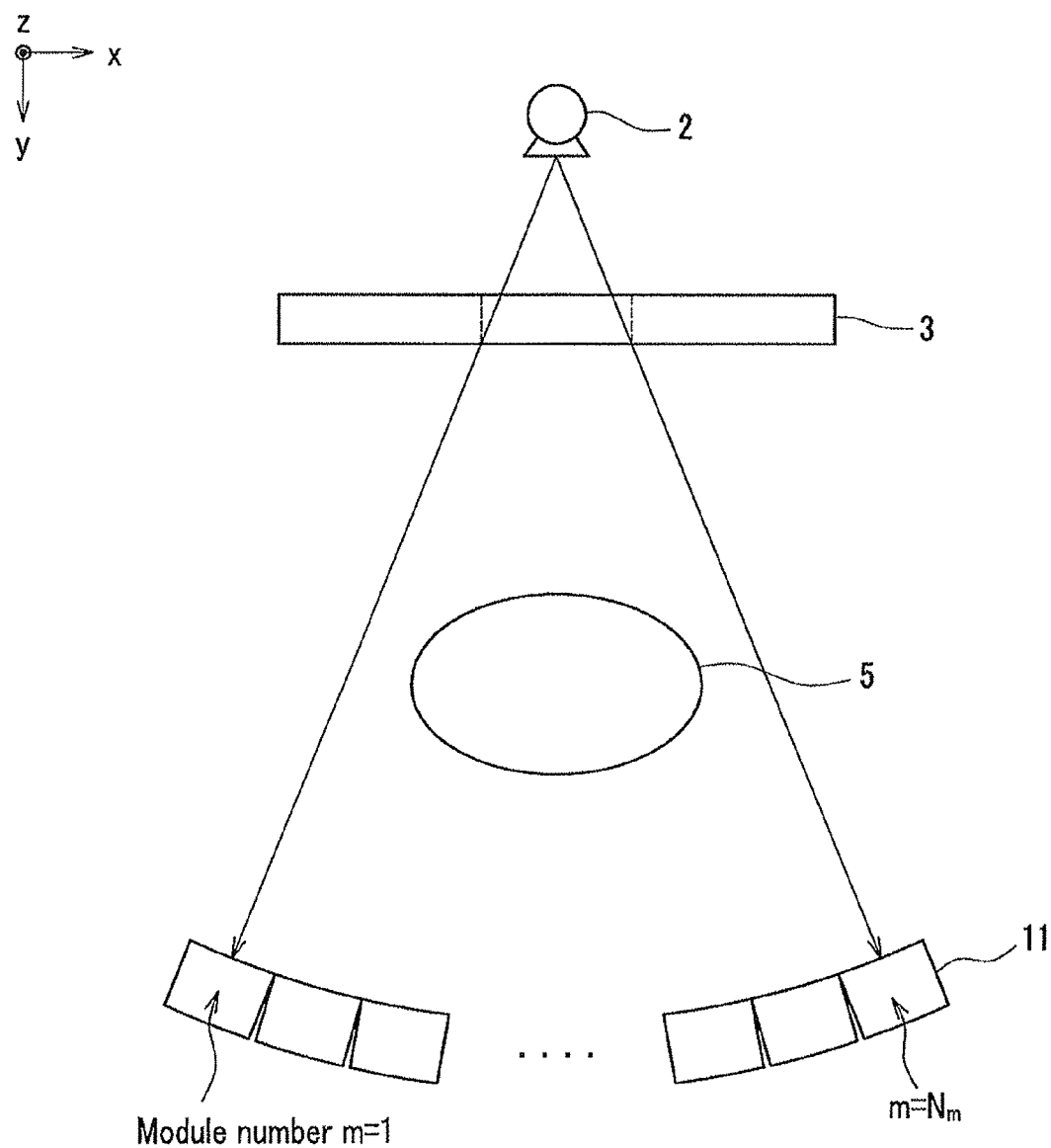
FIG. 3 is an illustration showing one example of arc-like arrangement of modules according to the first embodiment.

The detector 1 of the X-ray CT device 100 according to the present embodiment is mounted by a module unit. FIG. 2 is an illustration showing a module configured by the detector 1 and the one-dimensional grid 4. As shown in FIG. 2, $N_z$ pieces of detector 1 in z-direction and $N_x$ pieces of detector 1 in x-direction are arranged in a single detector module 11. FIG. 3 is an illustration showing one example of arrangement of modules in the X-ray CT device 100. As shown in FIG. 3, $N_m$ pieces of detector module 11 of the X-ray CT device 100 are disposed in an arc-like arrangement in x-direction.

Here, when the X-ray is radiated under the condition that the subject 5 is absent, an X-ray dose to be measured by the detector 1 is expressed by the following formula.

$$X(z, x, m, f) = I \cdot S(z, x, m) \cdot R(z, x, m, f) \quad \text{Formula 2}$$

In the Formula 2, I is an intensity of X-ray for irradiation, S is a specific sensitivity of the detector 1 for irradiated X-ray, and R is an X-ray incidence rate. m is a module number ($1 \leq m \leq N_m$) of the detector module 11, z is a detector number ($1 \leq z \leq N_z$) of the detector 1 in z-direction within the detector module 11 of a module number m, and x is a detector number ($1 \leq x \leq N_x$) of the detector 1 in x-direction within the detector module 11 of a module number m. In addition, f indicates a focal spot position in z-direction.

Figure 4:
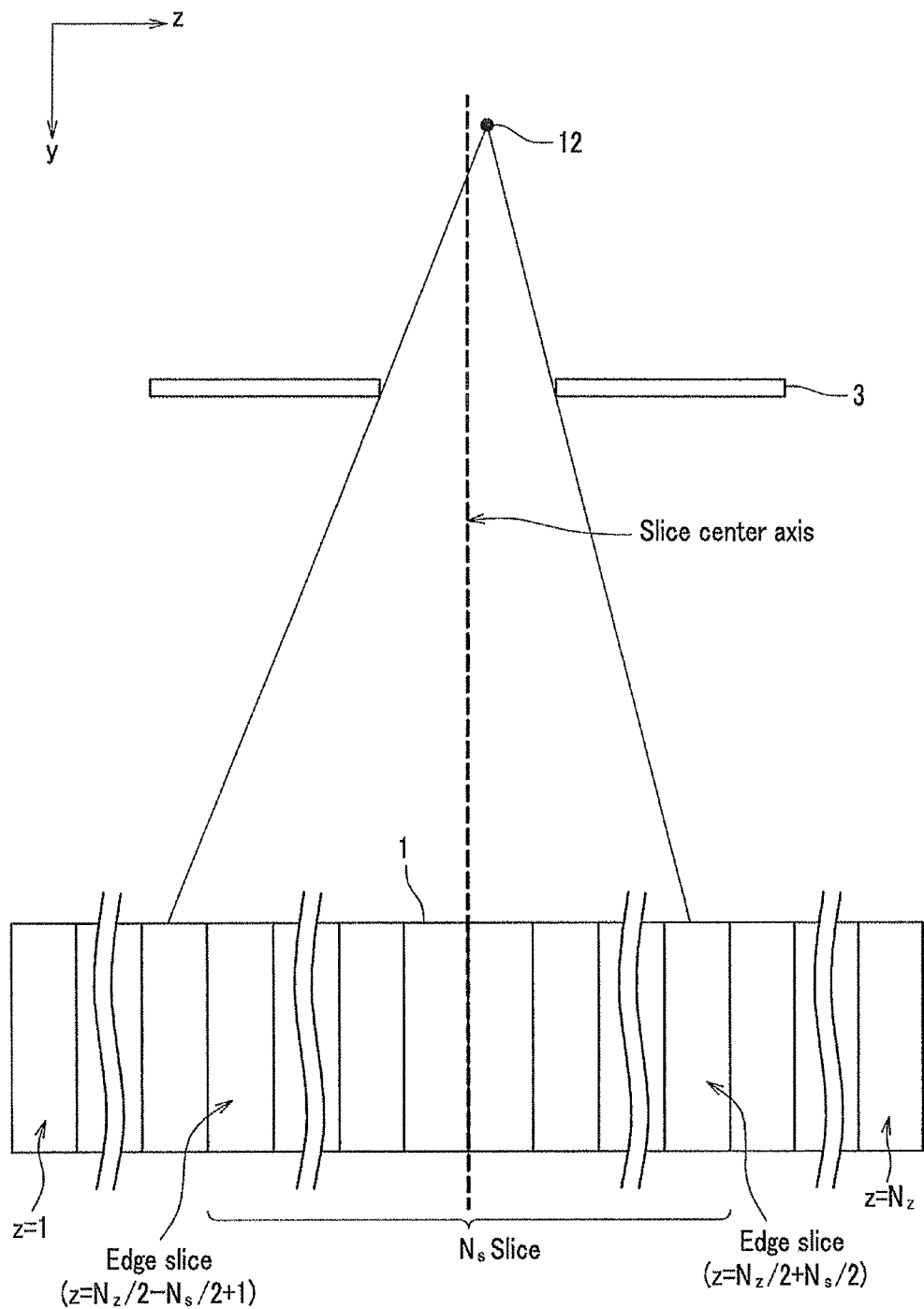
FIG. 4 is an illustration showing an X-ray irradiation area in $N_s$-slice collection according to the first embodiment.

Here, it is assumed that a scanning by the X-ray CT device 100 is performed at an $N_s$-slice scan mode using $N_s$ slices of the detector 1 arranged in x-direction. FIG. 4 is an illustration showing an X-ray irradiation area in the $N_s$-slice scan mode. A focal spot 12 in FIG. 4 is the X-ray tube 2 in FIG. 1. In the $N_s$-slice scan mode, the image reconstruction is performed using outputs of the detectors 1 in the slices from ($N_z/2-N_s/2+1$) to ($N_z/2+N_s/2$) in z-direction.

When a position of the focal spot 12 moves in z-direction, since the collimator 3 limits the irradiation area, an X-ray incidence rate R of the detector 1 in the edge slice ($N_z/2+N_s/2$) in z-direction becomes lower than 100%.

In addition, when the detector 1 is misaligned in z-direction, mismatch of focal spot position between measurement of the sensitivity collection data and the subject 5 data causes artifacts in the reconstructed image.

Figure 5A:
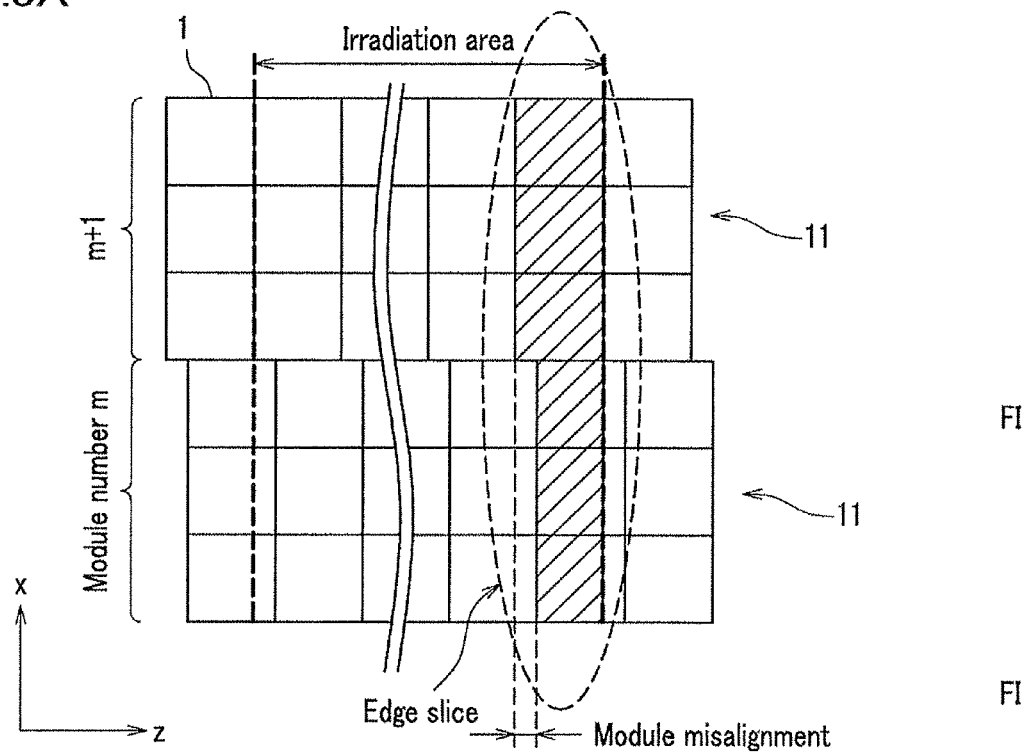
FIG. 5 is an illustration for explaining a change of an X-ray incidence rate due to movement of an irradiation area according to the first embodiment.
Figure 5B:
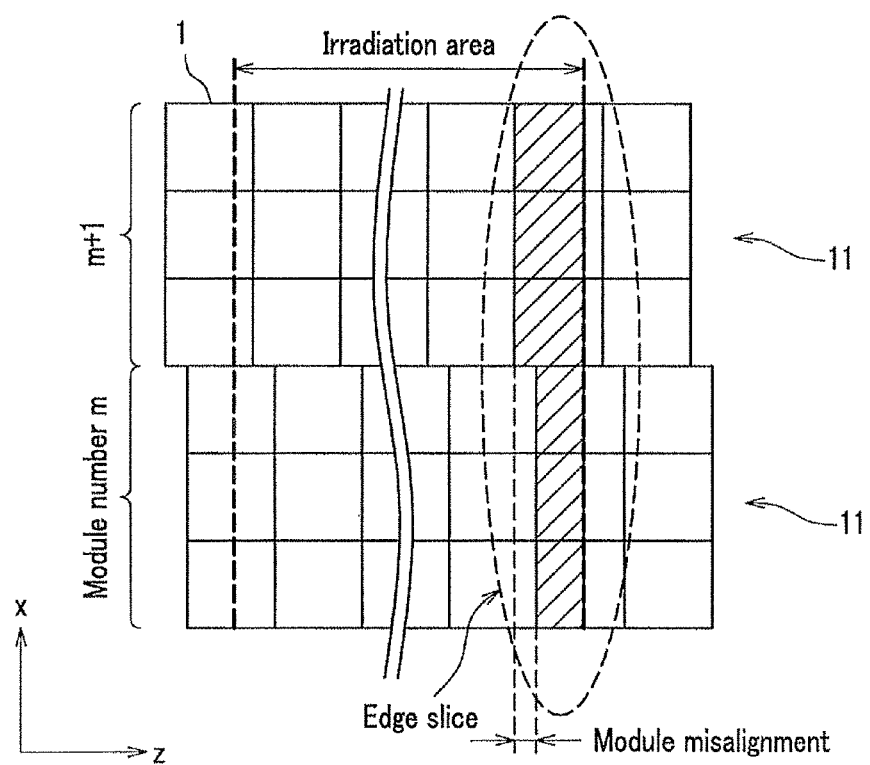

FIG. 5 is an illustration for explaining a change of the X-ray incidence rate due to movement of irradiation area. For example, in a detector module 11 of a module number (m+1) shown in FIG. 5A, there is no misalignment of the detector 1 in z-direction in the edge slice. However, in the detector module 11 of a module number m, misalignment of the detector 1 in z-direction changes an X-ray incidence rate of the detector in the edge slice, and as a result, artifact is generated in a reconstructed image. In addition, as shown in FIG. 5B, when a position of the focal spot 12 is moved in z-direction (see FIG. 4) and a position of the detector module 11 of a module number m is misaligned in z-direction, the x-ray incidence date is also changed, and as a result, artifact is also generated in the reconstructed image.

As described above, an actual misalignment of the detector 1 occurs by a module unit in many cases. Then, in the present embodiment, a case that the misalignment is generated by a detector module 11 is considered.

Therefore, the X-ray incidence rate R becomes a function that does not depend on a position in x-direction in the detector module 11, and Formula 3 becomes the following formula.

$$X(z,x,m,f)=I \cdot S(z,x,m) \cdot R(z,m,f) \qquad \text{Formula 3}$$

Namely, if the X-ray incidence rate R in the edge slice can be acquired by the detector module 11, the data that does not generate artifact can be acquired.

Next, explanations will be given of a method for acquiring an X-ray incidence rate R in another detector module 11 from the X-ray incidence rate R in a reference detector. The reference detector is a detector for directly detecting a radiated X-ray. Therefore, a detector 1 which is located at the edge portion in x-direction that has less chance to be covered by the subject 5 is used as a reference detector.

In the embodiment, detectors of reference numbers 1 to 4 in x-direction of the detector module 11 of a module number m=1 are set as a reference detector. For example, as an output of the reference detector in the edge slice ($z=N_z/2+N_s/2$) in a $N_s$-slice scan mode, an average value of four detectors 1 (if a module number of the detector module 11 shown in FIG. 2 is m=1, the four detectors 1 correspond to the detectors in box A when the number of slices is eight ($N_z=8$)) of m=1, $z=N_z/2+N_s/2$, and x=1 to 4 is used.

First, an aperture width of the collimator 3 is set to fully open, and a specific sensitivity correction data $X_{air}$ of the detector 1 is measured under the condition that the subject is absent. In this case, the X-ray incidence rate R becomes 100%, then, the specific sensitivity correction data $X_{air}$ becomes as follows.

$$X_{air}(z,x,m)=I \cdot S(z,x,m) \qquad \text{Formula 4}$$

where a focal spot position f of an output value X is omitted, assuming that an output of the detector 1 does not depend on the focal spot position.

Next, an aperture width of the collimator 3 is set to the aperture width in the $N_s$-slice scan mode, and when the measurement is performed by moving the focal spot position under the condition that the subject 5 is absent, an output value $X_f$ of the detector 1 is expressed by the following formula.

$$X_f(z,x,m,f)=I \cdot S(z,x,m) \cdot R(z,m,f) \qquad \text{Formula 5}$$

In the measurement of the output value $X_f$, the measurement may be performed by moving the focal spot 12 that is a position of the X-ray tube 2. However, a measurement data which is identical to the measurement data that is acquired by moving the focal spot 12 may be acquired by moving the collimator 3 in z-direction to change the irradiation area.

The X-ray incidence rate R can be calculated by the following formula, which is derived from Formula 4 and Formula 5.

$$R(z, m, f) = \frac{X_f(z, x, m, f)}{X_{air}(z, x, m)} \qquad \text{Formula 6}$$

Here, in order to increase in statistical accuracy, the X-ray incidence rate R may be calculated by an average in x-direction in the detector module 11

Next, an X-ray incidence rate R(z,m,f) for each detector module 11 is approximated by polynomial as follows, by using an X-ray incidence rate R(z, 1, f) of the detector module 11 (module number m=1) where a reference detector exists. Meanwhile, f indicates a focal point position in z-direction.

$$R(z, m, f) \approx \sum_{n=0}^{\infty} a_n \cdot R(z, 1, f)^n \qquad \text{Formula 7}$$

A coefficient $a_n$ in Formula 7 is the coefficient indicating a relationship between the X-ray incidence rate of the detector module 11 where a reference detector as a reference signal exists and the X-ray incidence rate for each detector module 11. Namely, if the coefficient an is acquired in advance by, for example, the least-square method, the X-ray incidence rate R for each detector module 11 may be estimated from Formula 7 by using the X-ray incidence rate R in the reference detector, even when the subject 5 is scanned. The coefficient $a_n$ is calculated in the edge slice ($z=N_z/2+N_s/2$) for each detector module 11 and stored in the storage unit 8. In other slice scan modes, the coefficient $a_n$ is also calculated in the edge slice for each detector module 11.

When the subject 5 is scanned, the X-ray incidence rate R in the reference detector can be acquired by dividing an output value X of the detector 1 by the specific sensitivity S and the X-ray intensity I. As shown in FIG. 4, in the N-slice scan mode, the X-ray intensity I in the slice {from (z=$N_z$/2−$N_s$/2+2) to (z=$N_z$/2+$N_s$/2−1) inside the edge slice ((z=$N_z$/2−$N_z$/2+1), (z=$N_z$/2+$N_s$/2} is not affected by position shifts of the focal spot 12 and the detector module 11. Therefore, the X-ray intensity I in the reference detector during the scanning of the subject 5 can be calculated from an output of the reference detector 1 of the inside slice {from (z=$N_z$/2−$N_s$/2+2) to (z=$N_z$/2+$N_s$/2−1}.

However, in a two-slice scan mode ($N_s$=2), the two slices {(z=$N_z$/2), (z=$N_2$/2+1} are edge slices, and since there is no inside slice, there is no detector output of the inside slice. Then, the X-ray intensity I is calculated as follows.

Figure 6:
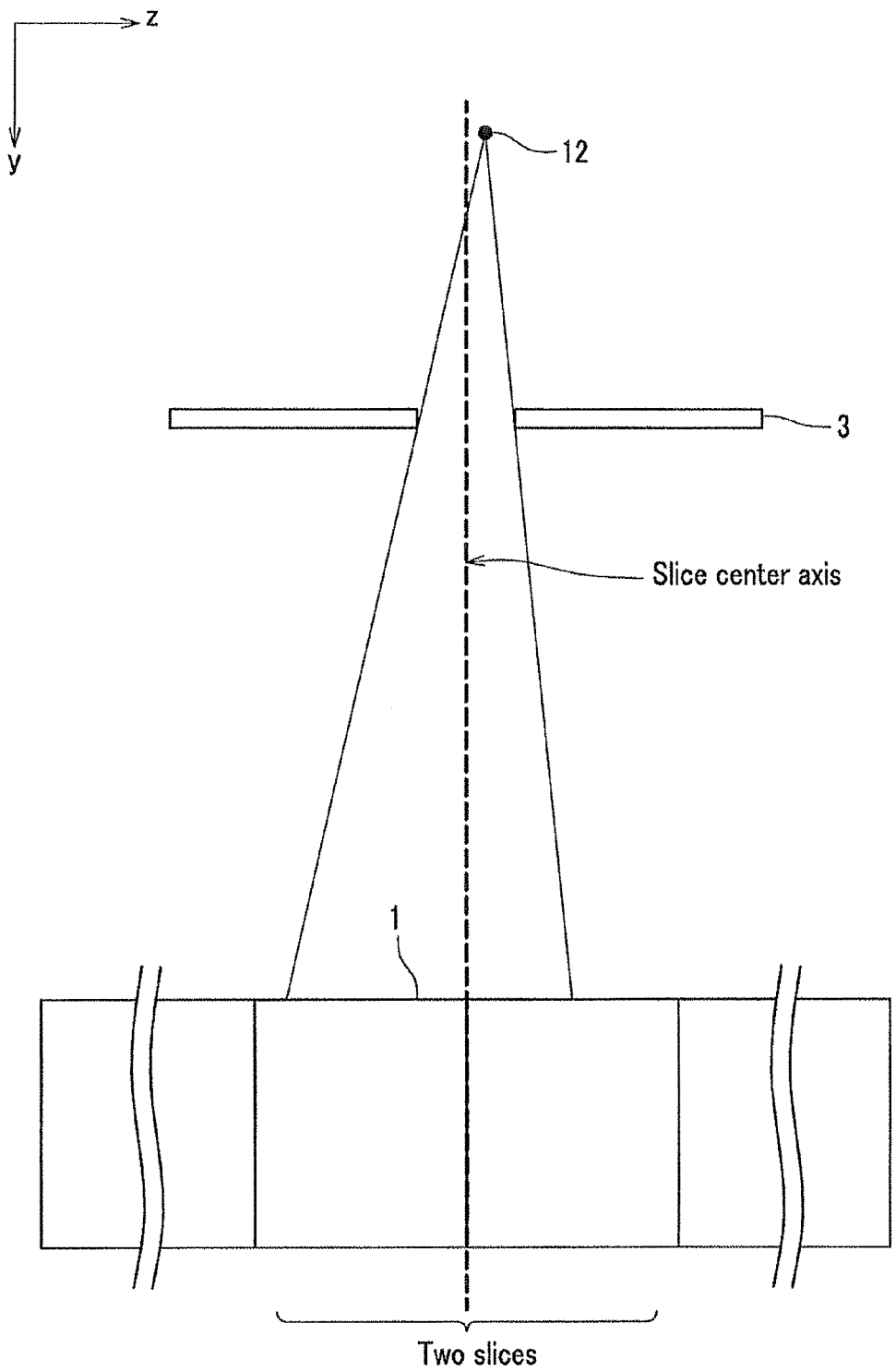
FIG. 6 is an illustration showing an irradiation area in two-slice collection according to the first embodiment.

FIG. 6 is an illustration showing an irradiation area in a two-slice collection mode.

First, an aperture width of the collimator 3 is set to the aperture width of the two-slice mode, an X-ray incidence rate R of a reference detector at a certain focal spot position f is calculated from Formula 6, and a value of integral $R_{sum}$ in z-direction is acquired. The value of integral $R_{sum}$ is a constant value that does not depend on the focal spot position f, and stored in the storage unit 8. If the X-ray intensity during the scanning of the subject 5 is denoted by $I_{patient}$, a value of integral $I_{sum}$ in z-direction after performing the specific sensitivity correction of the output of the reference detector at this time is expressed by ($I_{patient}$/I)×$R_{sum}$. Here, I is the X-ray intensity at the measurement of the specific sensitivity correction data. Therefore, by dividing the output of the reference detector after the specific sensitivity correction is performed by a value ($I_{patient}$/I), which is a value derived by dividing $I_{sum}$ by $R_{sum}$, the X-ray incidence rate R of the reference detector is acquired.

As described above, if the X-ray incidence rate R in the reference detector is calculated, an X-ray incidence rate for each detector module 11 can also be calculated, and by multiplying Formula 4 by the X-ray incidence rate, a sensitivity correction data X'$_{air}$ at each focal spot position can be acquired as shown in the following formula.

$$X'_{air}(z,x,m,f)=I \cdot S(z,x,m) \cdot R(z,m,f) \quad \text{Formula 8}$$

The image reconstruction processing unit 9 reconstructs an image after performing various kinds of corrections, such as a sensitivity correction using the sensitivity correction data X'$_{air}$ prepared by the pre-processing unit 7 and a CT value adjustment for the collection data detected by the detector 1 at each focal spot position, and the image display unit 10 displays the image.

In the present invention, since an X-ray incidence rate corresponding to a focal spot position is calculated by a continuous function as shown in Formula 7, an accuracy of the resultant sensitivity correction data X'$_{air}$ of Formula 8 also becomes high.

In addition, since the second-order approximation for the polynomial in Formula 7 is practically sufficient, the number of coefficient $a_n$ to be stored in the storage unit 8 can be reduced. In the methods described in Patent Document 1 and Patent Document 2, storage of correction data for each detector at each focal spot position is required. However, in the present invention, it is sufficient if the coefficient $a_n$ is stored in the storage unit 8.

In addition, in the method where a signal obtained by a reference detector is used as a reference signal, since effects of position shift of the collimator 3 and distortion due to the rotation are also included in the change of the X-ray incidence rate, an estimation of sensitivity correction data that can correct these effects as well as the focal spot movement can be performed.

In addition, a measurement of the X-ray incidence rate in Formula 6, namely, a calculation of the coefficient an may be performed at the installation of the device, and the measurement is performed for each parameter of a scanning speed and a tilt angle. In addition, when the detector module 11 and the X-ray tube 2 are replaced, the measurement of the X-ray incidence rate in Formula 6 is also performed.

In the measurement of a conventional sensitivity correction data, it is required to change an aperture width for each slice scan mode. However, in the present invention, only one measurement is required under the condition that the aperture width of the collimator is fully opened. Therefore, a frequency of daily measurement of the sensitivity correction data can be largely reduced.

The present invention may be combined with a method that moves the collimator 3 in accordance with a focal spot position, which is disclosed in Japanese Patent Publication No. 04-227238.

Next, explanations will be given of modified examples of the embodiment.

In the foregoing embodiment, a value of X-ray incidence rate for each detector module 11 is approximated by a value of a reference detector in the same slice, as shown by Formula 7. However, the value may be approximated as follows.

$$R(z, m, f) \approx \sum_{n=0}^{\infty} a'_n \cdot \left( \sum_{z'} R(z', 1, f) \right)^n \quad \text{Formula 9}$$

As shown by Formula 9, the value of the X-ray incidence rate may be approximated by a sum of X-ray incidence rate of a plurality of reference detectors in z-direction. In this case, an X-ray incidence rate of a reference detector during the scanning of the subject 5 is also acquired by the sum of the X-ray incidence rate of the plurality of reference detectors. The statistical accuracy can be improved by using the X-ray incidence rate that is added in z-direction.

In addition, as another modified example, there is a method that acquires an X-ray incidence rate of a reference detector during the scanning of the subject 5, by calculating an average in a view direction, that is, in a rotation direction of the detector 1. The statistical accuracy can be improved by acquiring an average of X-ray incidence rate of the number of views that can neglect the movement of the focal point.

In addition, in the foregoing embodiment, a module number m of the detector module 11 where a reference detector exists is m=1. However, a detector 1 of the detector module 11 whose module number m is m=$N_m$ may also be used as the reference detector. A reference detector to be used in the detector modules 11 is determined based on an output value of the detector 1. Namely, a threshold value is set in order to determine whether an X-ray entered into a reference detector has passed through the subject or not, and an output of the reference detector having the output higher (small attenuation) than the threshold vale is used.

If reference detectors of detector modules 11 of module numbers m=1 and m=$N_m$ are both effective, an X-ray incidence rate of another detector module 11 is acquired from the X-ray incidence rate of each of the reference detectors, and the sensitive correction data may be calculated using an average of the two X-ray incidence rates.

In addition, by utilizing the foregoing embodiment, a correction processing in a maximum slice collection mode may be executed.

Figure 7:
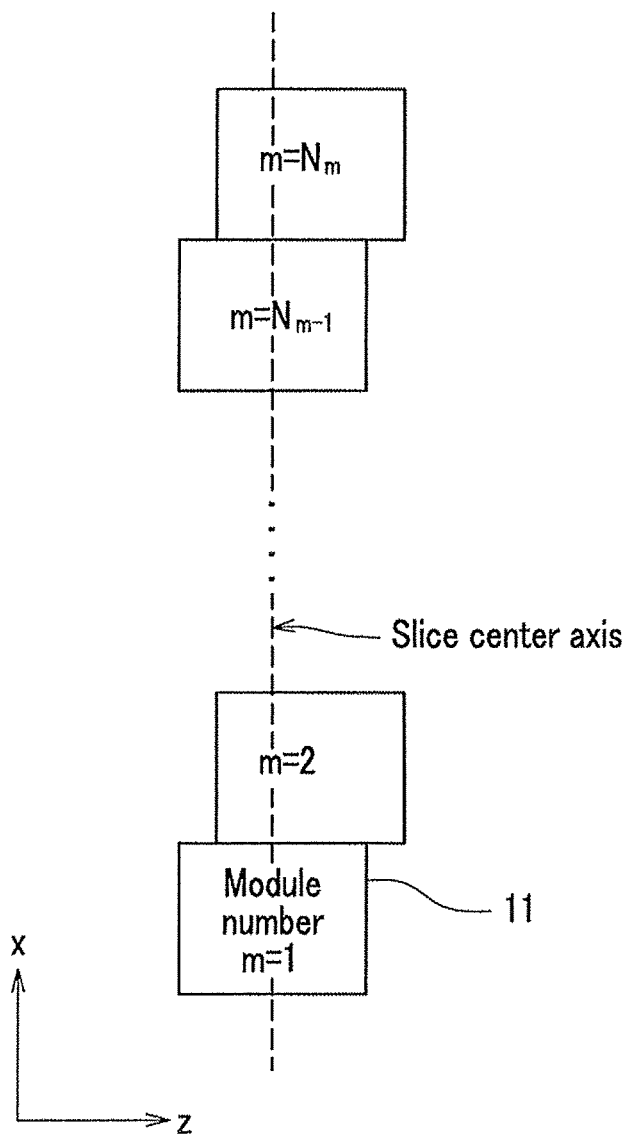
FIG. 7 is an illustration showing a module arrangement for correction in a maximum slice mode collection according to the first embodiment.

FIG. 7 is an illustration showing a module arrangement where detector modules 11 of module numbers m=1 and m=$N_m$ are intentionally shifted from the slice center axis when the detector module 11 is mounted on the device. By arranging the detector modules 11 as shown in FIG. 7, the foregoing embodiment becomes applicable even in the maximum slice collection mode. Since a shadow of the collimator 3 can be formed on a reference detector by shifting the detector module 11, an X-ray incidence rate of the reference detector and the X-ray incidence rate of another detector module 11 may be correlated to each other. In the example shown in FIG. 7, outputs of reference detectors in module numbers m=1 and m=$N_m$ are used for the X-ray incidence rates in detector numbers z=1 and z=$N_z$ in z-direction.

Second Embodiment

Next, explanations will be given of the second embodiment.

Figure 8:
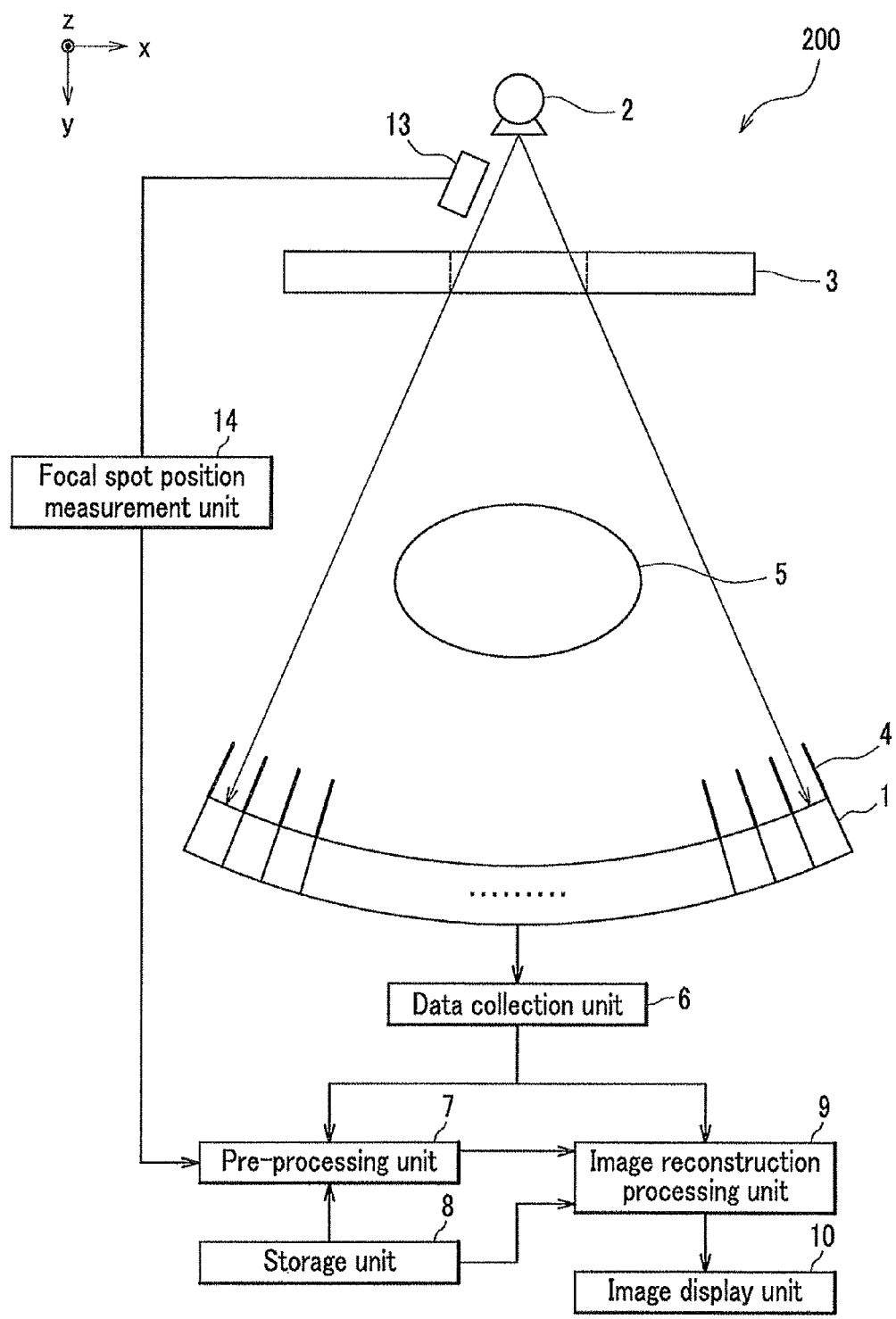
FIG. 8 is a schematic configuration view of an X-ray CT device according to a second embodiment of the present invention.

FIG. 8 is a schematic configuration view of an X-ray CT device 200 according to the second embodiment.

The X-ray CT device 200 includes a detector 1, an X-ray tube 2, a collimator 3, a one-dimensional grid 4, a data collection unit 6, a pre-processing unit 7, a storage unit 8, an image reconstruction processing unit 9, an image display unit 10, a focal spot position detector 13, and a focal spot position measurement unit 14.

The detector 1, the X-ray tube 2, the collimator 3, the one-dimensional grid 4, the data collection unit 6, the image reconstruction processing unit 9, and the image display unit 10 have identical configurations and functions to those of the X-ray CT device 100 shown in FIG. 1.

The focal spot position detector 13 detects a position of the X-ray tube 2 (focal point 12), and the focal spot position measurement unit 14 acquires a position coordinates of the focal spot.

The storage unit 8 stores a relationship between a focal spot position measured by the focal spot position measurement unit 14 and an X-ray incidence rate of the detector 1.

Next, explanations will be given of a method, which is executed in the pre-processing unit 7, for estimating a sensitivity correction data corresponding to a focal spot position.

A detector 1 of the X-ray CT device 200 is mounted by a module unit, and the detector 1 is arranged in one detector module 11 as shown in FIG. 2, as with the case of the X-ray CT device 100. The detector module 11 is arranged in an arc-like shape as shown in FIG. 3.

Here, in the X-ray CT device 200, a case where a misalignment is generated for each detector module 11 in the $N_s$-slice scan mode is considered.

In the case of the X-ray CT device 100, as shown by Formula 7, an X-ray incidence rate for each detector module 11 is expressed by the X-ray incidence rate in a reference detector. However, in the second embodiment, an X-ray incidence rate R for each detector module 11 is expressed by a focal spot position f. Namely, a focal spot position measured by the focal spot position detector 13 and by the focal spot position measurement unit 14 serves as a reference signal.

First, an aperture width of the collimator 3 is set to fully open, and a specific sensitivity of the detector 1 is measured under the condition that the subject 5 is absent (Formula 4). Next, the aperture width of the collimator 3 is set to the aperture width of $N_s$-slice scan mode, and the specific sensitivity of the detector 1 is measured under the condition that the subject 5 is absent, while moving the focal spot position f (Formula 5). In this case, the focal spot position f is simultaneously measured by the focal spot position detector 13 and the focal spot position measurement unit 14. Then, Formula 6 is derived by Formula 4 and Formula 5.

Next, the X-ray incidence rate R for each detector module 11 is approximated by polynomial by using the focal spot position f.

$$R(z, m, f) \approx \sum_{n=0}^{\infty} b_n \cdot f^n \qquad \text{Formula 10}$$

A coefficient $b_n$ in Formula 10 is the coefficient indicating a relationship between the focal spot position f, which is a reference signal, and the X-ray incidence rate R for each detector module 11. Namely, if the coefficient $b_n$ is calculated in advance by, for example, the least-square method and stored in the storage unit 8, the X-ray incidence rate R for each detector module 11 can be estimated from Formula 10 by using each focal spot position f, even when the subject 5 is scanned.

In other slice scan modes, the coefficient $b_n$ is also calculated for each detector module 11 in the edge slice.

By multiplying Formula 4 by the calculated X-ray incidence rate R, a sensitivity correction data corresponding to a focal spot position is prepared. The measured data is reconstructed into an image after various kinds of corrections, such as a sensitivity correction using the sensitivity correction data corresponding to the focal spot position f and a CT value adjustment are performed in the image reconstruction processing unit 9, and the image is displayed by the image display unit 10.

In the second embodiment, since an X-ray incidence rate corresponding to a focal spot position is calculated by a continuous function as shown in Formula 10, an accuracy of the resultant acquired sensitivity correction data $X'_{air}$ becomes also high.

In addition, since the second-order approximation for the polynomial in Formula 10 is practically sufficient, the number of coefficient $b_n$ to be stored in the storage unit 8 can be reduced.

In addition, the coefficient $b_n$ may be acquired, for example, when the device is installed.

The second embodiment may be combined with a method that moves the collimator 3 in accordance with a focal spot position, which is disclosed in Japanese Patent Publication No. 04-227238.

When the X-ray incidence rate R for each detector module 11 shown in Formula 10 is measured, the center of aperture of the collimator 3 is located on the slice center axis. Therefore, when the collimator 3 is moved in accordance with the movement of the focal spot, a focal spot position f' corresponding to the time when the center of aperture of the collimator exists on the slice center axis is calculated from the measured focal spot position f and the center position of aperture of the collimator, and the f' is substituted into Formula 10 in order to calculate the X-ray incidence rate R for each detector module 11. From the X-ray incidence rate R, a sensitivity correction data for each view corresponding to the focal spot position is calculated.

In the method for moving the collimator 3, there may be a possibility to cause a delay in completing the movement of the collimator 3 after a movement of the focal spot is detected and an instruction of movement of the collimator 3 is issued. Effects of an irradiation area shift caused by the delay of the control can be reduced by performing the sensitivity correction using a sensitivity correction data for each view after the data collection is completed.

Third Embodiment

Next, explanations will be given of the third embodiment.

Figure 9:
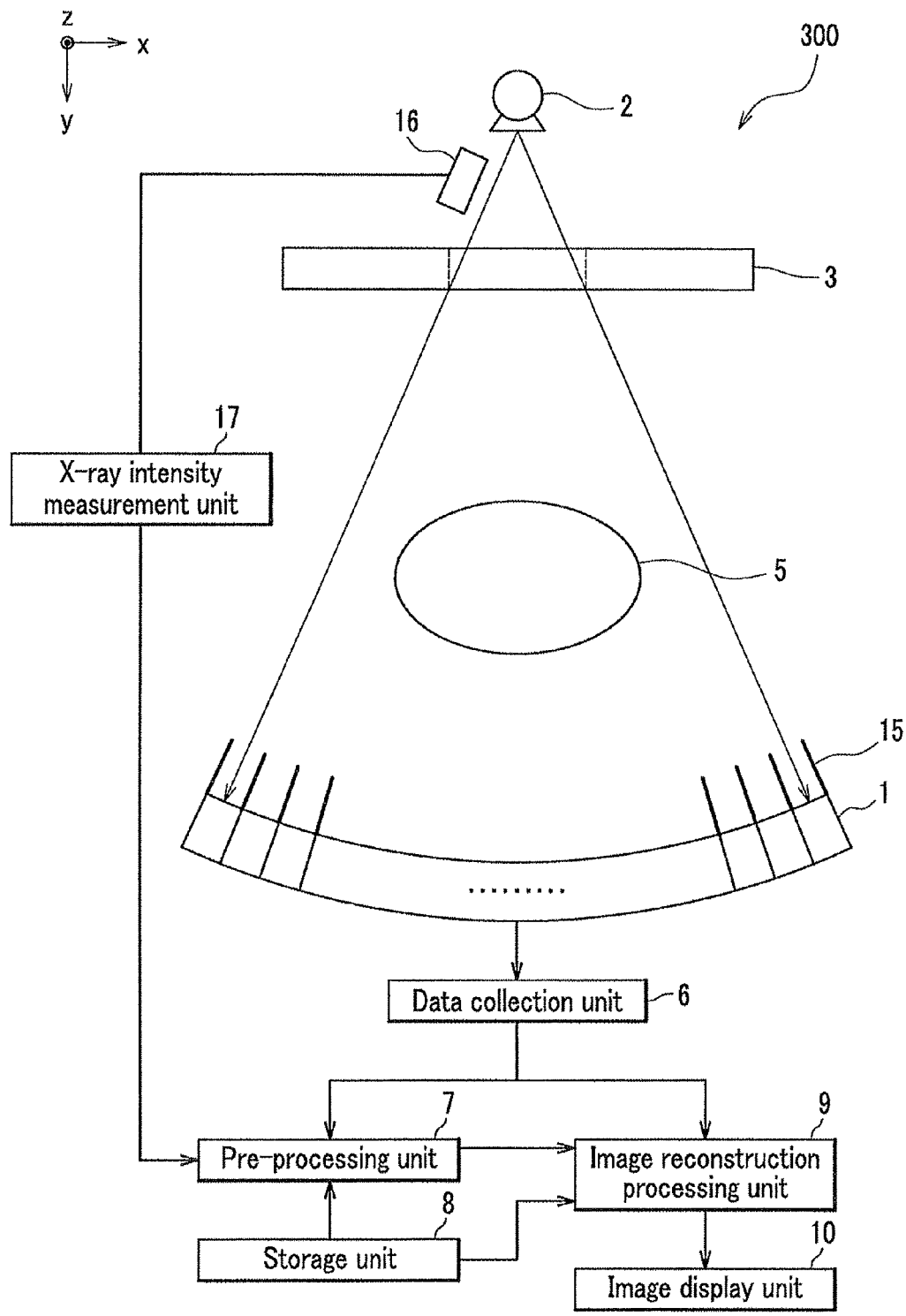
FIG. 9 is a schematic configuration view of an X-ray CT device according to a third embodiment of the present invention.

FIG. 9 is a schematic configuration view of an X-ray CT device 300 according to the third embodiment.

The X-ray CT device 300 includes a detector 1, an X-ray tube 2, a collimator 3, a data collection unit 6, a pre-processing unit 7, a storage unit 8, an image reconstruction processing unit 9, an image display unit 10, a two-dimensional grid 15, an X-ray intensity detector 16, and an X-ray intensity measurement unit 17.

The detector 1, the X-ray tube 2, the collimator 3, the data collection unit 6, the storage unit 8, the image reconstruction processing unit 9, and the image display unit 10 have identical configurations and functions to those of the X-ray CT device 100 shown in FIG. 1.

The two-dimensional grid 15 removes scattered rays in x-direction and z-direction which are generated from the subject 5.

The X-ray intensity detector 16 detects an X-ray intensity for irradiation and the X-ray intensity measurement unit 17 measures the X-ray intensity.

Next, explanations will be given of a method, which is executed in the pre-processing unit 7, for estimating a sensitivity correction data corresponding to a focal spot position.

Figure 10:
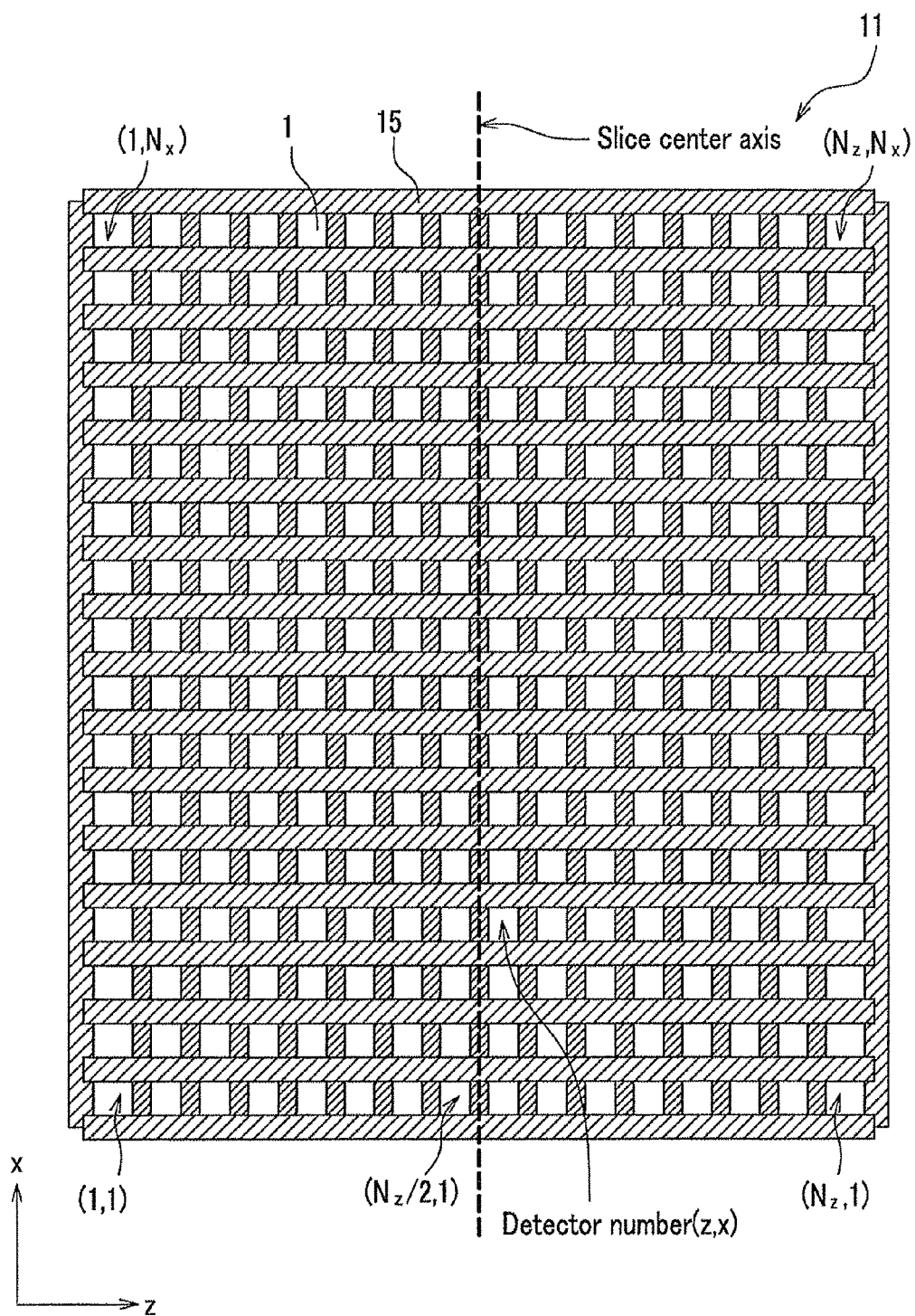
FIG. 10 is an illustration showing a module configured by detectors and a two-dimensional grid according to the third embodiment.

The detector 1 of the X-ray CT device 300 is mounted by a module unit. FIG. 10 is an illustration showing a detector module 11 configured by detectors and a two-dimensional grid. As shown in FIG. 10, $N_z$ detectors 1 in z-direction and $N_x$ detectors 1 in x-direction are arranged in a single detector module 11. In addition, the two-dimensional grid 15 for removing the scattered rays in x-direction and z-direction, which are generated from the subject 5, is mounted in front of the detector 1.

In addition, as shown in FIG. 3, $N_m$ detector modules 11 in the X-ray CT device 300 are arranged in an arc-like shape in x-direction.

In the foregoing first and second embodiments, only the X-ray incidence rate in the edge slice to be shadowed by the collimator 3 is considered. However, in the third embodiment, since a shadow by the two-dimensional grid 15 is also generated by the movement of the focal spot, X-ray incidence rates in all slices are acquired.

Hereinafter, in the X-ray CT device 300, a case where a misalignment is generated for each detector module 11 in the scanning of $N_s$-slice scan mode is considered.

Explanations will be given of a method for acquiring an X-ray incidence rate for each slice in other detector modules 12 from the X-ray incidence rate of a reference detector, by disposing the reference detector in the detector module 11 of a module number m=1, as with the first embodiment.

First, an aperture width of the collimator 3 is set to fully open, and a specific sensitivity of the detector 1 is measured under the condition that the subject 5 is absent. In this case, since a focal spot position is not necessarily located on the slice center axis, an output $X_{air}$ of the detector becomes a function depending on the focal point position f, as shown by the following formula.

$$X_{air}(z,x,m,f_{air}) = I \cdot S(z,x,m) \cdot R(z,m,f_{air}) \quad \text{Formula 11}$$

Here, $f_{air}$ is a focal point position when a specific sensitivity S is measured, and the X-ray incidence rate at the position is denoted by $R(z, m, f_{air})$"

Next, an aperture width of the collimator 3 is set to the aperture width in the $N_s$-slice scan mode, and the specific sensitivity of the detector 1 is measured under the condition that the subject 5 is absent, while moving the focal spot position. Then, the output $X_f$ of the detector 1 at the focal spot position f becomes as follows.

$$X_f(z,x,m,f) = I \cdot S(z,x,m) \cdot R(z,m,f) \quad \text{Formula 12}$$

Here, R(z,m,f) is an X-ray incidence rate at the focal spot position f.

From Formula 11 and Formula 12, an X-ray incidence rate R' is expressed by the following formula.

$$R'(z, m, f) = \frac{R(z, m, f)}{R(z, m, f_{air})} = \frac{X_f(z, x, m, f)}{X_{air}(z, x, m, f_{air})} \quad \text{Formula 13}$$

Next, the X-ray incidence rate R' (z,m,f) for each detector module 11 is approximated by the following polynomial using an X-ray incidence rate R' (z, 1, f) of the detector module 11 of a module number m=1 where a reference detector exists.

$$R'(z, m, f) \approx \sum_{n=0}^{\infty} c_n \cdot R'(z, 1, f)^n \quad \text{Formula 14}$$

A coefficient $c_n$ in Formula 14 is the coefficient indicating a relationship between an X-ray incidence rate of the detector module 11 where a reference detector as a reference signal exists and an X-ray incidence rate for each detector module 11. Namely, if the coefficient $c_n$ is calculated in advance by, for example, the least-square method, the X-ray incidence rate R' for each detector module 11 can be estimated from Formula 14 by using the X-ray incidence rate R' in the reference detector, even when the subject 5 is scanned. The coefficient $c_n$ is calculated for each slice in each detector module 11 and stored in the storage unit 8. In addition, in other slice scan modes, the coefficient $c_n$ is also calculated for each slice in each detector module 11.

When the subject 5 is scanned, the X-ray incidence rate R' of the reference detector is calculated by dividing an output value X of the detector by the specific sensitivity S and the X-ray intensity I. The X-ray intensity I is measured by the X-ray intensity detector 16 and the X-ray intensity measurement unit 17.

If the X-ray incidence rate R' in the reference detector is calculated as described above, the X-ray incidence rate R' in each detector module 11 can also be calculated, and by multiplying Formula 11 by the X-ray incidence rate R', a sensitivity correction data $X'_{air}$ for each focal spot position is calculated as follows.

$$X'_{air}(z,x,m,f) = I \cdot S(z,x,m) \cdot R(z,m,f) \quad \text{Formula 15}$$

The image reconstruction processing unit 9 reconstructs an image after performing various kinds of corrections, such as a sensitivity correction using the sensitivity correction data $X'_{air}$ prepared by the pre-processing unit 7 and a CT value adjustment for the collection data detected by the detector 1 at each focal spot position, and the image display unit 10 displays the image.

As described above, in the third embodiment, since the X-ray incidence rate corresponding to a focal spot position is calculated by a continuous function as shown in Formula 14, an accuracy of the resultant acquired sensitivity correction data $X'_{air}$ becomes also high.

In addition, since the second-order approximation for the polynomial in Formula 14 is practically sufficient, the number of coefficient $c_n$ to be stored in the storage unit 8 can be reduced.

In the foregoing method, an X-ray intensity I during the scanning of the subject 5 is acquired by the X-ray intensity detector 16 and the X-ray intensity measurement unit 17. However, the X-ray intensity may be acquired by other methods.

Figure 11:
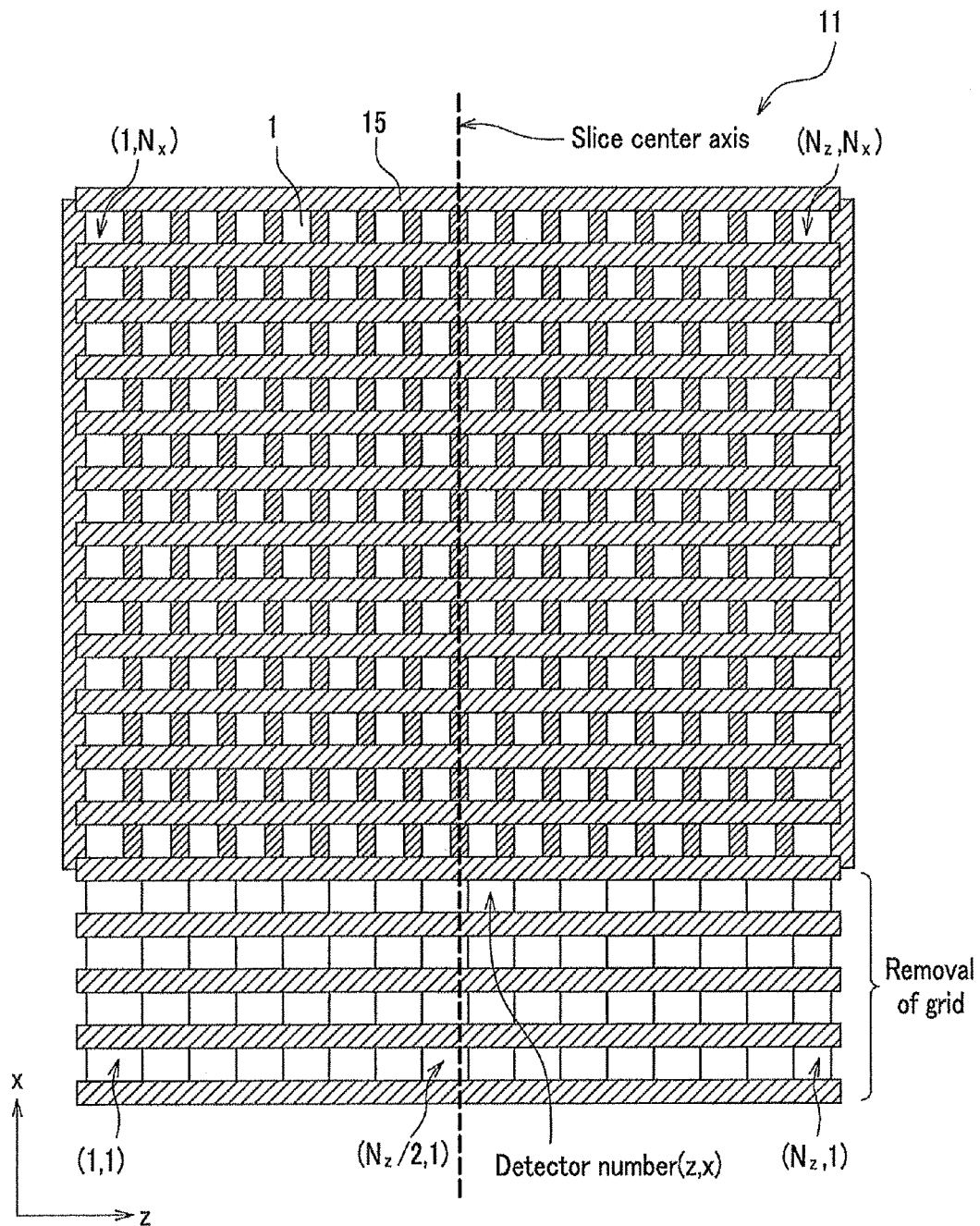
FIG. 11 is an illustration showing a module where a part of a two-dimensional grid is removed according to the third embodiment.

FIG. 11 is an illustration showing a detector module 11 that is configured by a two-dimensional grid where a detector and a part of the grid are removed.

As shown in FIG. 11, by removing a grid that removes scattered rays against a reference detector in the detector module 11 of a module number m=1, the X-ray intensity I can be measured by the reference detector. In this case, the reference detector of the module number m=1 where a part of the grid is removed as shown in FIG. 11 is used for the measurement of the X-ray intensity I, and the X-ray incidence rate R' indicated by Formula 13 may be acquired by a reference detector in the module number m=$N_m$.

Fourth Embodiment

Next, explanations will be given of the fourth embodiment.

Figure 12:
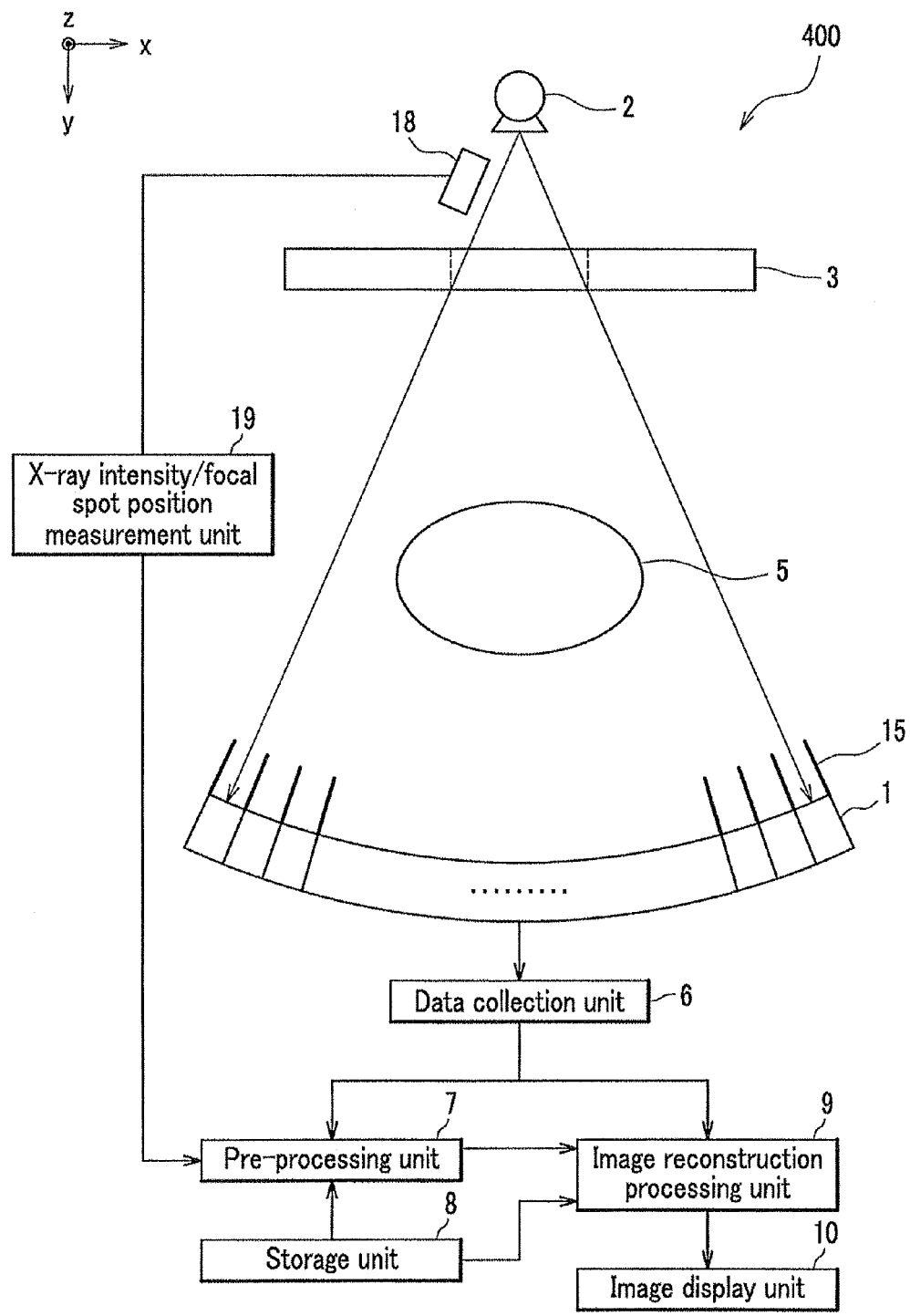
FIG. 12 is a schematic configuration view of an X-ray CT device according to a fourth embodiment of the present invention.

FIG. 12 is a schematic configuration view of an X-ray CT device 400 according to the fourth embodiment.

The X-ray CT device 400 includes a detector 1, an X-ray tube 2, a collimator 3, a data collection unit 6, a pre-processing unit 7, a storage unit 8, an image reconstruction processing unit 9, an image display unit 10, a two-dimensional grid 15, an X-ray intensity/focal spot position detector 18, and an X-ray intensity/focal spot position measurement unit 19.

The detector 1, the X-ray tube 2, the collimator 3, the data measurement unit 6, the image reconstruction processing unit 9, and the image display unit 10 have identical configurations and functions to those of the X-ray CT device 100 shown in FIG. 1.

The two-dimensional grid 15 removes scattered rays in x-direction and z-direction which are generated when the subject 5 is irradiated by the X-ray, and a structure thereof is shown in FIG. 10.

The X-ray intensity/focal spot position detector 18 detects a position (focal spot position) of the X-ray tube 2 and X-ray intensity, and the X-ray intensity/focal spot position measurement unit 19 measures the position (focal spot position) of the X-ray tube 2 and the X-ray intensity radiated from the X-ray tube 2.

Next, explanations will be given of a method, which is executed in the pre-processing unit 7, for estimating a sensitivity correction data corresponding to a focal spot position.

The detector 1 of the X-ray CT device 400 is mounted by a module unit. Similar to the detector module 11 shown in FIG. 10, $N_z$ detectors 1 in z-direction and $N_x$ detectors 1 in x-direction are arranged in a single detector module 11 of the X-ray CT device 400. In addition, the two-dimensional grid 15 for removing scattered rays in x-direction and in z-direction, which are generated from the subject 5, is mounted in front of the detector 1.

In addition, as shown in FIG. 3, $N_m$ detector modules 11 in the X-ray CT device 400 are arranged in an arc-like shape in x-direction.

In the X-ray CT device 400, as with the X-ray CT device 300, since a shadow by the two-dimensional grid 15 is generated by the movement of the focal spot, X-ray incidence rates in all slices are acquired.

Hereinafter, in the X-ray CT device 400, a case where a misalignment is generated in each detector module 11 in the $N_s$-slice scan mode is considered, and explanations will be given of a method for calculating an X-ray incidence rate for each slice in each detector module 11 from the measured focal spot position.

First, an aperture width of the collimator 3 is set to fully open, and a specific sensitivity of the detector 1 is measured under the condition that the subject 5 is absent (Formula 11). Next, the aperture width of the collimator 3 is set to the opening with in the $N_s$-slice scan mode, and the specific sensitivity of the detector 1 is measured by moving a focal spot position f under the condition that the subject is absent (Formula 12). At this time, the focal spot position f is simultaneously measured by the X-ray intensity/focal spot position detector 18 and the X-ray intensity/focal spot position measurement unit 19. Then, Formula 13 is obtained from Formula 11 and Formula 12.

Next, the X-ray incidence rate R' in each detector module 11 is approximated by polynomial as follows by using the focal spot position f.

$$R'(z, m, f) \approx \sum_{n=0}^{\infty} d_n \cdot f^n \qquad \text{Formula 16}$$

A coefficient $d_n$ in Formula 16 is the coefficient indicating a relationship between the focal spot position f of a reference signal and the X-ray incidence rate R for each detector module 11. Namely, if the coefficient $d_n$ is calculated in advance by, for example, the least-square method and stored in the storage unit 8, the X-ray incidence rate R' for each detector module 11 can be estimated from Formula 16 using each focal spot position f, even when the subject 5 is scanned.

The coefficient $d_n$ is acquired for each slice in each detector module 11 and stored in the storage unit 8. In addition, in other slice scan modes, the coefficient $d_n$ is also acquired for each slice in each detector module 11.

By multiplying Formula 11 by a value of the X-ray incidence rate R' which is acquired from Formula 16, a sensitivity correction data $X'_{air}$ for each focal spot position can be calculated as follows.

$$X'_{air}(z,x,m,f) = I \cdot S(z,x,m) \cdot R(z,m,f) \qquad \text{Formula 17}$$

Here, the X-ray intensity I is measured by the X-ray intensity/focal spot position detector 18 and the X-ray intensity/focal spot position measurement unit 19.

As described above, a measured data detected by the detector 1 at each focal spot position f is corrected by the pre-processing unit 7 according to the foregoing processing as the sensitivity correction data $X'_{air}$, and outputted to the image reconstruction processing unit 9. The image reconstruction processing unit 9 reconstructs an image after performing various kinds of corrections such as a CT value adjustment for the sensitivity correction data $X'_{air}$, and the image display unit 10 displays the image.

As described above, in the fourth embodiment, since the X-ray incidence rate corresponding to a focal spot position is calculated by a continuous function as shown in Formula 16, an accuracy of the resultant acquired sensitivity correction data $X'_{air}$ becomes also high.

In addition, since the second-order approximation for the polynomial in Formula 16 is practically sufficient, the number of coefficient $d_n$ to be stored in the storage unit 8 can be reduced.

In addition, the coefficient $d_r$ may be measured and stored when the device is installed.

REFERENCE DESCRIPTION

1 Detector
2 X-ray tube
3 Collimator
4 One-dimensional grid
5 Subject
6 Data collection unit
7 Pre-processing unit
8 Storage unit
9 Image reconstruction processing unit
10 Image display unit
11 Detector module (Detection module)
12 Focal spot
13 Focal spot position detector
14 Focal spot position measurement unit
15 Two-dimensional grid
16 X-ray intensity detector
17 X-ray intensity measurement unit
18 X-ray intensity/focal spot position detector
19 X-ray intensity/focal spot position measurement unit

What is claimed is:

1. An X-ray Computed Tomography (CT) device, comprising:
   an X-ray tube that radiates an X-ray;
   a collimator that limits an irradiation area of the X-ray;
   at least one detection module that has a plurality of detectors configured to detect the X-ray;
   a grid that is disposed in the plurality of detectors and removes scattered rays from a subject when the X-ray is radiated on the subject, wherein a one-dimensional grid that removes scattered rays in a direction perpendicular to a slice direction is used as the grid; and
   a storage unit;
   a pre-processing unit configured to prepare a sensitivity correction data based on an output of the plurality of detectors;
   an image reconstruction processing unit configured to correct the output of the plurality of detectors by using the sensitivity correction data and reconstructs an image of the subject based on the corrected output;
   and an image display unit configured to display the image reconstructed by the image reconstruction processing unit, wherein the pre-processing unit comprises:
   a unit configured to acquire an X-ray incidence rate of each detection module at each focal spot position by changing the focal spot position that is a position of the X-ray tube under a condition that the subject is absent;
   a unit configured to acquire a relationship between a reference signal and the acquired X-ray incidence rate of each detection module under the condition that the subject is absent;
   a unit configured to store acquired relationship in the storage unit;
   a unit configured to calculate the X-ray incidence rate of each detection module during scanning of the subject by using the reference signal during the scanning of the subject and the stored relationship when the subject is scanned;
   and a unit configured to acquire the sensitivity correction data of each focal spot position by using the calculated X-ray incidence rate during the scanning of the subject wherein when a scanning of the subject by a plural slice scan mode is performed, the sensitivity correction data of the each focal spot position is acquired in an edge slice.

2. The X-ray CT device according to claim 1, wherein the acquired X-ray incidence rate in each detection module at each focal spot position is approximated by a polynomial of the reference signal; and wherein the relationship is expressed by a coefficient of the polynomial.

3. The X-ray CT device according to claim 1, wherein an output of a detector that detects the X-ray which travels a path without the subject is used for the reference signal.

4. The X-ray CT device according to claim 1, wherein a value indicating the focal spot position is used for the reference signal.

5. An X-ray CT device, comprising:
   an X-ray tube that radiates an X-ray;
   a collimator that limits an irradiation area of the X-ray;
   at least one detection module that has a plurality of detectors configured to detect the X-ray;
   a grid that is disposed in the plurality of detectors and removes scattered rays from a subject when the X-ray is radiated on the subject, wherein a two-dimensional grid that removes scattered rays in a slice direction and in a direction perpendicular to the slice direction is used as the grid; and
   a storage unit;
   a pre-processing unit configured to prepare a sensitivity correction data based on an output of the plurality of detectors;
   an image reconstruction processing unit configured to correct the output of the plurality of detectors by using the sensitivity correction data and reconstructs an image of the subject based on the corrected output;
   and an image display unit configured to display the image reconstructed by the image reconstruction processing unit, wherein the pre-processing unit comprises: a unit configured to acquire an X-ray incidence rate of each detection module at each focal spot position by changing the focal spot position that is a position of the X-ray tube under a condition that the subject is absent;
   a unit configured to acquire a relationship between a reference signal and the acquired X-ray incidence rate of each detection module under the condition that the subject is absent;
   a unit configured to store acquired relationship in the storage unit;
   a unit configured to calculate the X-ray incidence rate of each detection module during scanning of the subject by using the reference signal during the scanning of the subject and the stored relationship when the subject is scanned;
   and a unit configured to acquire the sensitivity correction data of each focal spot position by using the calculated X-ray incidence rate during the scanning of the subject, wherein when a scanning of the subject by a plural slice scan mode is performed, the sensitivity correction data of the each focal spot position is acquired in all slices.

* * * * *